(12) United States Patent
Ebner

(10) Patent No.: US 6,755,837 B2
(45) Date of Patent: Jun. 29, 2004

(54) APPARATUS AND METHOD FOR HARVESTING BONE

(75) Inventor: Peter R. Ebner, Hollis, NH (US)

(73) Assignee: Maxilon Laboratories, Inc., Amherst, NH (US)

( * ) Notice: Subject to any disclaimer, the term of this patent is extended or adjusted under 35 U.S.C. 154(b) by 45 days.

(21) Appl. No.: 10/252,874

(22) Filed: Sep. 23, 2002

(65) Prior Publication Data

US 2004/0059338 A1 Mar. 25, 2004

(51) Int. Cl.$^7$ ................................ A61B 17/32
(52) U.S. Cl. ................... 606/84; 606/170; 600/570
(58) Field of Search .................. 606/79, 83, 84, 606/85, 110, 114, 131, 132, 161, 170; 600/562, 570, 571

(56) References Cited

U.S. PATENT DOCUMENTS

| | | |
|---|---|---|
| 2,526,662 A | 10/1950 | Hipps et al. |
| 4,366,822 A | 1/1983 | Altshuler |
| 4,466,429 A | 8/1984 | Loscher et al. |
| 4,722,338 A | 2/1988 | Wright et al. |
| 4,798,213 A | 1/1989 | Doppelt |
| 4,844,064 A | 7/1989 | Thimsen et al. |
| 4,994,024 A | 2/1991 | Falk |
| 5,052,411 A | 10/1991 | Schoolman |
| 5,133,359 A | 7/1992 | Kedem |
| 5,269,785 A | 12/1993 | Bonutti |
| 5,403,317 A | 4/1995 | Bonutti |
| 5,683,406 A * | 11/1997 | Altobelli et al. ............ 606/170 |

FOREIGN PATENT DOCUMENTS

WO    WO 97/11646    3/1997

* cited by examiner

Primary Examiner—David O. Reip
(74) Attorney, Agent, or Firm—Hayes Soloway P.C.

(57) ABSTRACT

A bone grafting and/or shaping instrument includes a handle portion, a collection chamber and a blade. Features on the blade cooperate with features on the collection chamber to secure the blade to the collection chamber. A flexible joint between the collection chamber and the handle portion allows the user to orient the cutting edge of the blade in any desired position relative to the handle portion.

74 Claims, 4 Drawing Sheets

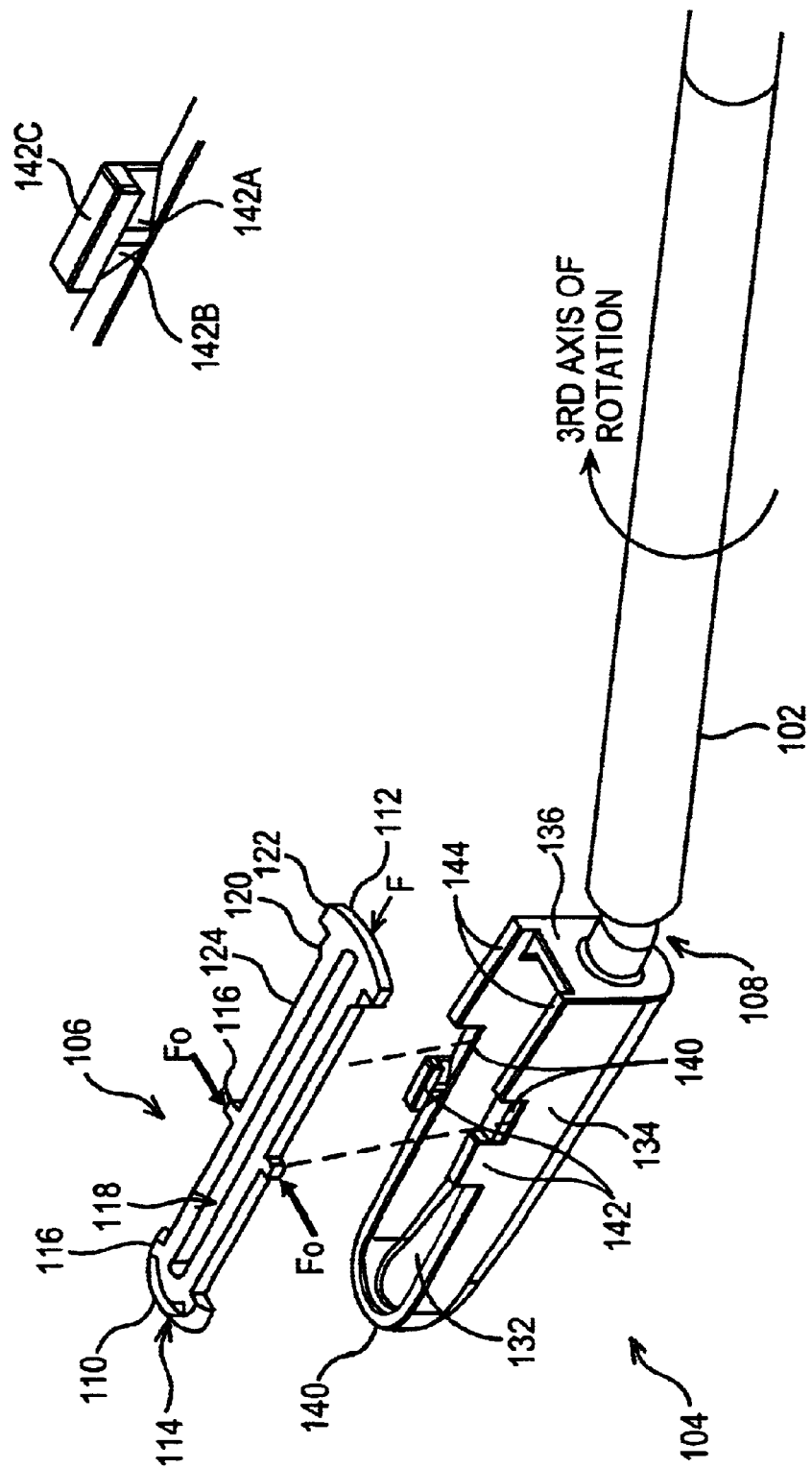

APPARATUS AND METHOD FOR HARVESTING BONE

FIELD OF THE INVENTION

The present invention relates to the field of surgery. The invention has particular utility in connection with the removal and collection of bone from the surface of one or more donor sites, and the preparation and placement of the autogenous bone material at a second location in the patient, e.g. for use in grafting bone to osseous deficiencies, such as periodontal and dentoalveolar defects, bone deficiencies around dental implants, and numerous orthopedic applications that require grafting, and will be described in connection with such utility, although other utilities are contemplated.

BACKGROUND OF THE INVENTION

Many reconstructive procedures used in medicine and dentistry involve the manipulation and healing of bones. Such procedures may involve changes in the position, orientation, shape and size of skeletal structures. A problem that is commonly encountered during such procedures is a lack of bone graft material. Bone graft material may be used in several applications, such as to fill between sections of bone that have been repositioned, to change surface geometry, or to add bone to an area that is deficient, such as in conjunction with periodontal surgery or dental implants in the patients' jaws.

The need to harvest small bone grafts from intraoral sites has been common in periodontal surgery to restore bone defects around teeth. In the case of dental implant surgery, bone grafts may be needed to augment atrophic alveolar ridges of the maxilla and/or mandible and the sinus floor to increase the dimension of these bone sites to accommodate and totally cover the endosseus portion of implant fixtures. Bone grafts also are used in conjunction with guided tissue regeneration; a technique that uses a membrane to isolate hard tissue from soft tissue sites and potentiates hard tissue healing.

It is often difficult to harvest adequate amounts of autogenous bone from intraoral sites. Therefore, clinicians often rely on non-autogenous sources of graft material, such as bone from cadaver sources (homologous or allogenic grafts), animal sources (heterogenous or xenogeneic grafts), or synthetic bone substitutes. However, healing of non-autogenous material grafts is not as extensive or predictable as healing of autogenous bone; plus there is the additional cost of such non-autogenous graft materials, which can be significant.

Clinicians use several techniques to remove bone for grafting for intraoral procedures. In one such technique rotary instruments, such as side cutting burrs or trephines, are used to remove a piece or section of cortical bone from a local intraoral site in the maxilla or mandible. The cortical bone is often morsalized into a particulate form, either manually with a rongeur like instrument or in a bone mill. The particulate bone is then combined with blood to form an osseous coagulum, which is then positioned and packed into the osseous defect around the teeth or implant. See Robinson, R.E. "Osseous Coagulum for Bone Induction", J. Periodontology 40:503(1969). Suction devices with filters have been fabricated and manufactured to collect the bone dust from rotary instruments. See Hutchinson, RA "Utilization of an Osseous Coagulum Collection Filter", J. Periodontology 44:668(1973). See also Goldman, et al., "Periodontal Therapy", pp 994–1005, C.V. Mosby Co., (1980); and Haggarty, et al., "Autogenous Bone Grafts: A Revolution in the Treatment of Vertical Bone Defects", J. Periodontology 42:626(1971). While such techniques are widely used by clinicians, the techniques have limitations, since sites to harvest sections of intraoral bone are limited in number and extent because of limited intraoral access, proximity to tooth roots, nerve structures and sinus cavities, and thin plates of bone.

Other techniques for harvesting bone include using chisels or osteotomes to remove and manually collect shavings from the surface. These instruments must be very sharp and the process is often awkward and time consuming. Other manual instruments such as bone files and rasps also remove bone. However, the efficiency of cutting and the ability to use the removed bone is greatly limited. Another technique is to collect bone dust generated by twist drills or taps used to prepare the sites for implant placement. However, much of the bone material may be lost while the site is being irrigated to cool the cutting instrument. When larger amounts of bone are needed for major reconstructive procedures, other sites such as the hip (anterior or posterior ilium), tibia, ribs, or the calvarium often are used. However, using such other sites necessitates a second surgical site, which may require postoperative hospitalization, and thus is less amenable, e.g. in the case of an out-patient dental procedure.

Various surgical devices have been proposed and/or are in use to harvest bone marrow samples for biopsy or devices such as rongeurs or bone cutters or punches to remove sections or convex edges of bone. Surgical devices also are in use in arthroscopy and endoscopy for cutting or drilling bone or tissue and removing the tissue fragments. Ultrasonic devices to cut bone also are in use; however, such devices require the removal of the irrigant and debris liberated by the apparatus. Each of these methods and/or devices, however, suffers from one or more deficiencies as applied to the collection of bone for grafting.

Yet other patented devices have been proposed; each of these, however, suffers from one or more deficiencies:

U.S. Pat. Nos. 5,403,317 and 5,269,785 to Bonutti show a method and apparatus for the percutaneous cutting and removal of tissue fragments from human. The Bonutti device removes the tissue fragments by suction where it can be collected and then placed elsewhere in the patient from where originally obtained. Bonutti employs a flexible drill, and suction to remove the debris to an externally placed collection reservoir, where it is compressed before being replaced into the patient.

U.S. Pat. No. 2,526,662 to Hipps discloses a bone meal extractor apparatus for mechanically removing bone meal from a donor bone site through a small percutaneous site using a drill. The drill shavings, which comprise primarily sub-surface bone, are then evacuated into an open cut that the drill passes through, for collection.

U.S. Pat. No. 4,798,213 to Doppelt teaches a device for obtaining a bone biopsy for diagnosis of various bone diseases. The Doppelt device is intended to remove a core of bone using a tubular drill, while maintaining the architecture of the tissue. The sample is obtained from the marrow space and not intended from re-implantation.

U.S. Pat. No. 5,133,359 to Kedem shows a hard tissue biopsy instrument in which samples are taken using a rotatably driven hollow needle.

U.S. Pat. No. 4,366,822 to Altshuler discloses a method and apparatus for bone marrow cell separation and analysis.

The Altshuler apparatus collects bone marrow cells in a filtration chamber on a filter interposed between a needle directed into the bone marrow site and an aspirator or vacuum source, i.e. using negative pressure to withdrawal marrow cells through a needle.

U.S. Pat. No. 5,052,411 to Schoolman teaches, a vacuum barrier attachment for shielding the operator of a medical tool from harmful aerosols and blood, etc. created by drilling, sawing types of actions, etc. The Schoolman device requires vacuum and is not intended for harvesting tissue for re-implantation.

U.S. Pat. No. 4,722,338 to Wright et al. discloses a device instrument for removing bone that uses a shearing action similar to a rongeur to cut bone, with means for collecting fragments of bone as they are removed. The Wright et al. device reportedly is used mainly for the removal of projections or edges of bone using a shearing mechanism without the intent of harvesting the bone for grafting.

U.S. Pat. No. 4,994,024 to Falk teaches an arthroscopy hook-clippers device that allows the unobstructed removal of tissue or bone with removal of the fragments by suction. The Falk device is intended for arthroscopy applications and with the removal of projections of tissue or bone and not specifically for the harvest of tissue for grafting.

Yet other prior art devices are disclosed in U.S. Pat. No. 4,466,429 to Loscher et al. and U.S. Pat. No. 4,844,064 to Thimsen et al.

The foregoing discussion of the prior art derives from my earlier PCT Application No. WO 97/11646, which describes a hand-held surgical instrument for the cutting, removal, and storage of bone surface shavings for use as autogenous bone grafts. The instrument is comprised of a blade mounted in a handle for holding and supporting said blade. The blade has a cutting structure adjacent its distal end. In a preferred form, the handle cooperates to provide a storage space adjacent the distal end of the blade for receiving harvested bone from the cutting structure. The instrument is held at an acute angle to the bone, and with minimal downward pressure, is drawn across the bone surface to cut and collect a thin shaving of bone. The blade is preferably retractable to allow the clinician access to harvested material. A plunger preferably is incorporated into the handle to serve both as a locking mechanism to secure the blade and as a means to advance and consolidate the bone in the distal aspect of the instrument.

The present invention provides enhanced functionality and reduced cost over the surgical instrument described in my aforesaid PCT Application No. WO 97/11646.

SUMMARY OF THE INVENTION

The invention is directed to a hand-held surgical instrument for the cutting, removal, and storage of bone surface shavings for use as autogenous bone grafts. The instrument is comprised of a blade and storage compartment coupled to a handle. The blade may be made from a section of metal that is oriented relative to a longitudinal axis of the handle to allow the operator to more easily cut or scrape and accumulate bone. The blade preferably is slid into place over a collection chamber and secured to prevent accidental removal. The collection chamber includes storage space adjacent the cutting edge of the blade for receiving harvested bone from the blade. The collection chamber may be coupled to a handle portion at a joint. The joint allows the user to orient the blade relative to the handle in order to access hard to reach locations. A pry bar may be employed to assist in removal of the blade from the collection chamber. The pry bar may be stored within the handle portion.

In use, the blade and collection chamber is held at an acute angle to the bone and the user applies a minimal downward pressure as the tool is drawn across the bone surface. Thin shavings of bone are cut by the cutting edge and collected in the collection chamber. The clinician can view the amount of harvested material through an opening, preferably a slot, provided in the blade.

In a preferred embodiment, the blade is removable and replaceable, while the handle is reusable.

In another preferred embodiment of the invention, the handle has an area of reduced mechanical strength or a flexible joint displaced from the cutting edge, the area of reduced mechanical strength allowing the cutting edge to be angularly positioned relative to a longitudinal axis of the blade.

The above and other objects, features, and advantages of the present invention will be apparent in the following detailed description thereof when read in conjunction with the appended drawings wherein the same reference numerals denote the same or similar parts, and wherein:

BRIEF DESCRIPTION OF THE DRAWINGS

FIG. 2 is an exploded view of the bone-harvesting instrument of FIG. 1;

FIG. 5 is a an exploded view of a portion of the bone-harvesting instrument of FIG. 1;

DETAILED DESCRIPTION OF PREFERRED EMBODIMENTS

Figure 1:
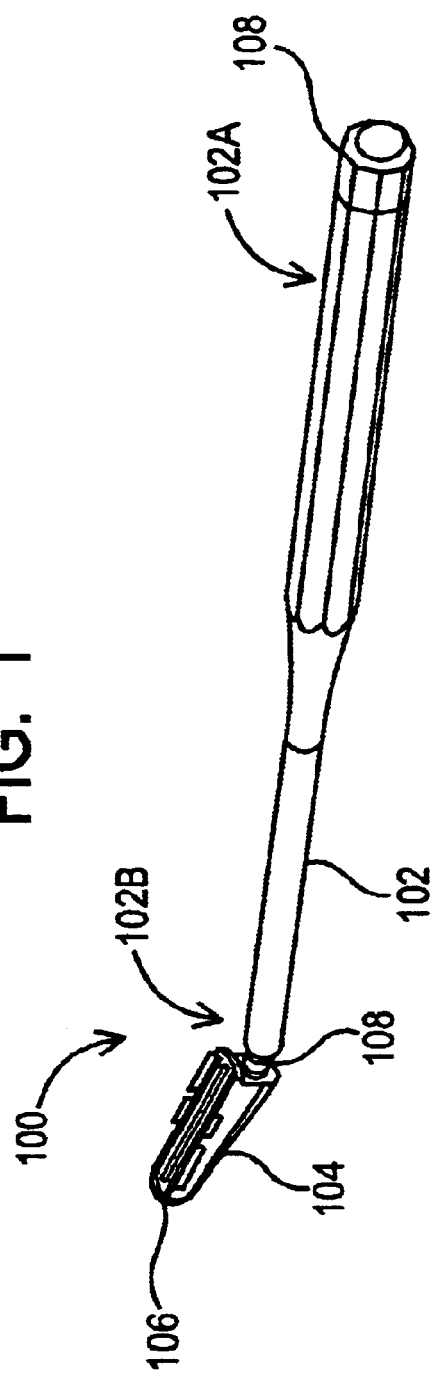
FIG. 1 is a perspective view of an exemplary bone-harvesting instrument consistent with the present invention.

FIG. 1 shows a bone-harvesting instrument 100. The instrument 100 may have a handle portion 102, a collection chamber 104 and a blade 106. The handle portion 102 may have a first end 102A and a second end 102B. The handle portion 102 may have a removable end cap 150 in close proximity to the first end 102A for storage of a blade removal tool 200 (see FIG. 3). In one embodiment, the collection chamber 104 may be coupled to the handle portion 102 through a flexible joint 108. In a preferred embodiment of the invention, the flexible joint is an area of reduced mechanical strength. The area of reduced mechanical strength allows the cutting edge of the blade to be angularly and/or rotationally positioned to a desired angle and/or position relative to a longitudinal axis of the blade 106. In another embodiment, the flexible joint may be a ball and socket joint.

The area of reduced mechanical strength may be an area where the thickness is less than the thickness of a surrounding area. Alternatively, the area of reduced mechanical strength may be an area where the material has a lower yield strength than the surrounding area. The area of reduced mechanical strength allows the collection chamber 104 to flex relative to the handle portion 102.

FIG. 2 shows an exploded view of the instrument 100 with the blade 106 spaced from the collection chamber 104.

The collection chamber 104 preferably is a five-sided enclosure with a bottom 132, sidewalls 134 and an end wall 136. The interior volume of the collection chamber 104 may be used to hold accumulated bone shavings. The collection chamber 104 preferably is formed of stainless steel. Alternatively, collection chamber 104 may be molded from a polymeric material, preferably a medical grade plastic. The depth of the collection chamber 104 at the end opposite the end wall 136 preferably is less than the depth near the end wall 136. This allows the instrument to be used to access hard-to-reach locations.

A top surface 140 of the sidewall 134 defines a generally planar surface for supporting at least the cutting end of the blade 106. Extending from the top surface 140 may be a pair of opposing upstanding retainer members 142 and a pair of opposing stabilizing members 144. The retainer members 142 help secure the blade 106 to the collection chamber 104 during use and the stabilizing members 144 prevent the blade 106 from rotating. Each retainer member 142 includes a first cam surface 142A, a second cam surface 142B, and a ledge portion 142C (see FIG. 5). The ledge portion 142C helps maintain the blade 106 in contact with the top surface 140 and the cam surfaces 142A and 142B help resist linear movement of the blade 106. The ledge preferably is spaced from the top surface 140 approximately the thickness of the blade 106.

In an alternative embodiment, a single pair of cam surfaces located on one side of the collection chamber are used to resist the linear movement of the blade 106.

In an alternative embodiment, a single stabilizing member, for example a post upwardly extending from the end wall 136, cooperates with an opening in the blade 106 to prevent rotation of the blade 106.

The blade 106 may be stamped or machined from metal, preferably stainless steel, or other suitable materials with similar hardness. The blade 106 has a first end 110, a second end 112, a middle section 124 and at least one outwardly extending lobe 116, preferably a pair of outwardly extending lobes. The first end 110 includes an aperture 116 adjacent at least a portion of a cutting edge 114. Thus, the cutting edge 114 is drawn along a surface, generated shavings pass through the aperture 116 and are accumulated in the collection chamber 104. An opening 118 extends along a longitudinal axis of the blade 106. The opening 118 allows the user to visually check the amount of accumulated material and also provides a spring force to allow lobe/s 116 on the blade 106 to move inward to allow the blade 106 to pass the upstanding retainer members 142 on the collection chamber 104.

The second end 112 includes a stop mechanism 120 that prevents the blade 106 from traveling past its intended "use" position (see FIG. 3) and a protrusion 122 that can be used to help extract the blade 106 from the collection chamber 104.

To couple the blade 106 to the collection chamber 104, the user first aligns the lobe/s 116 in the space between the upstanding retainer members 142 and the stabilizing member/s 144. The user then applies a force (F) to the end surface of the blade 106 and directs the force along the longitudinal axis of the blade 106 towards the end wall 136. The longitudinal force causes the lobe/s 116 on the blade 106 to contact the cam surface/s 142A on the retainer member 142 of the collection chamber 104. The cam surface/s 142A applies a compressive force ($F_o$) to the lobe/s 116 urging the lobe/s towards the centerline of the blade 106. The user continues to apply a longitudinal force to the blade 106 until the stop mechanism 120 on the blade 106 contacts the end wall 136 of the collection chamber 104. The blade is now in the "use" position. In the "use" position, the lobe/s 116 preferably are partially returned to their original "relaxed" position so as to maintain a retaining force on cam surface 142B.

Figure 4:
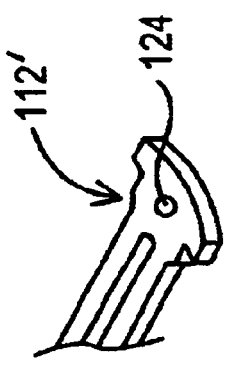
FIG. 4 is a perspective view of a portion of a second embodiment blade consistent with the present invention.
Figure 3:
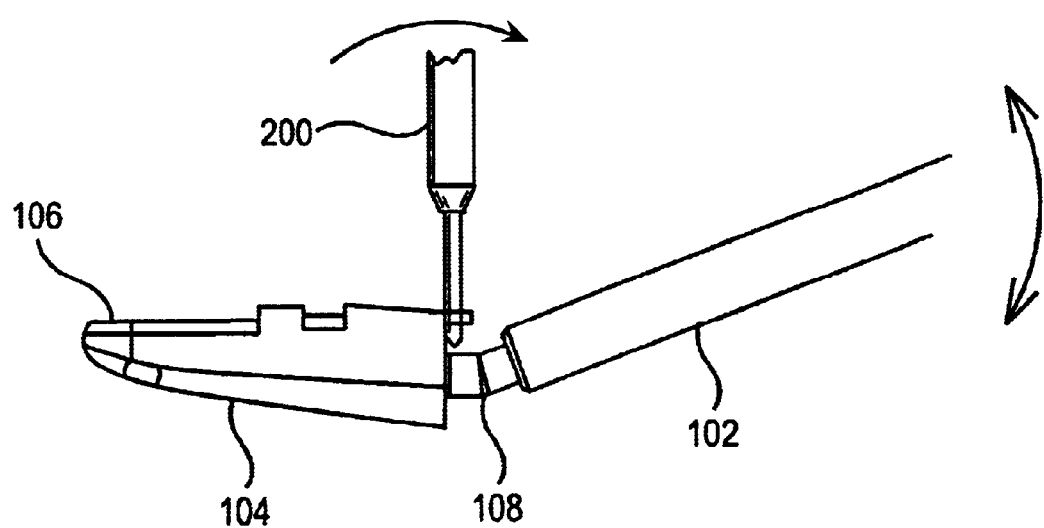
FIG. 3 is a profile view of the bone-harvesting instrument of FIG. 1.

A tool 200, as shown in FIG. 3, may be inserted between the protrusion 122 and the end wall 136 to decouple the blade 106 from the collection chamber 104. The tool 200 includes one, and preferably two prongs coupled to a handle. The prongs are spaced a distance greater than the width of the stop mechanism 120, but narrower than the width of the protrusion 122. Alternatively, a pry bar may be inserted through an opening 124 (as shown in FIG. 4) in an end 112' of a blade to extract the blade 106 from the collection chamber 104.

In an alternative embodiment, a blade may be inserted from the end opposite the end wall 136 and urged towards the end wall 136. The collection chamber may include a stop mechanism that contacts a portion of the cutting end of the blade.

Figure 7:
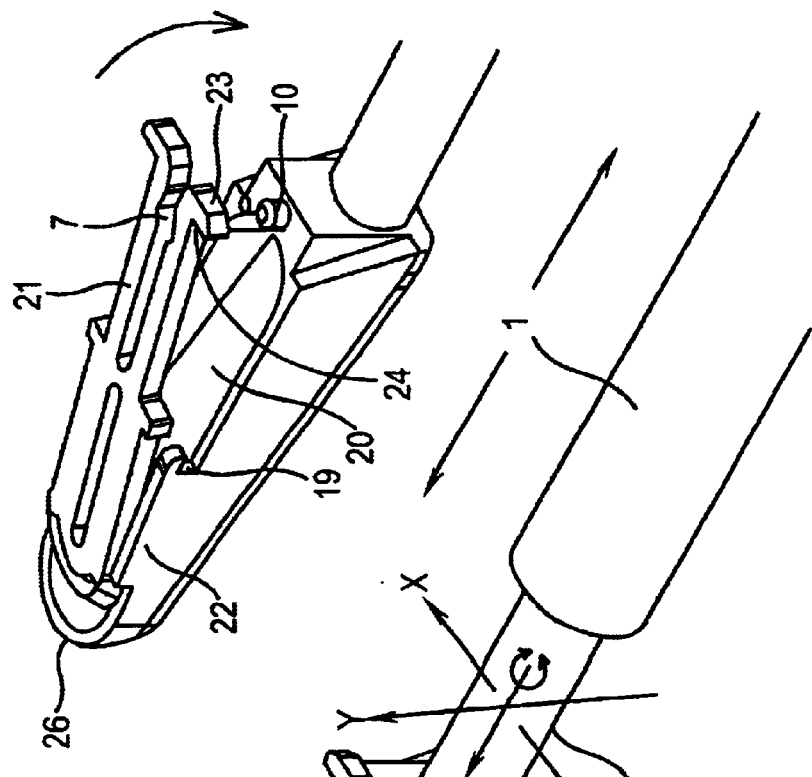
FIG. 7 is a view similar to FIG. 6, and illustrating loading of a blade into the handle of the instrument.
Figure 6:
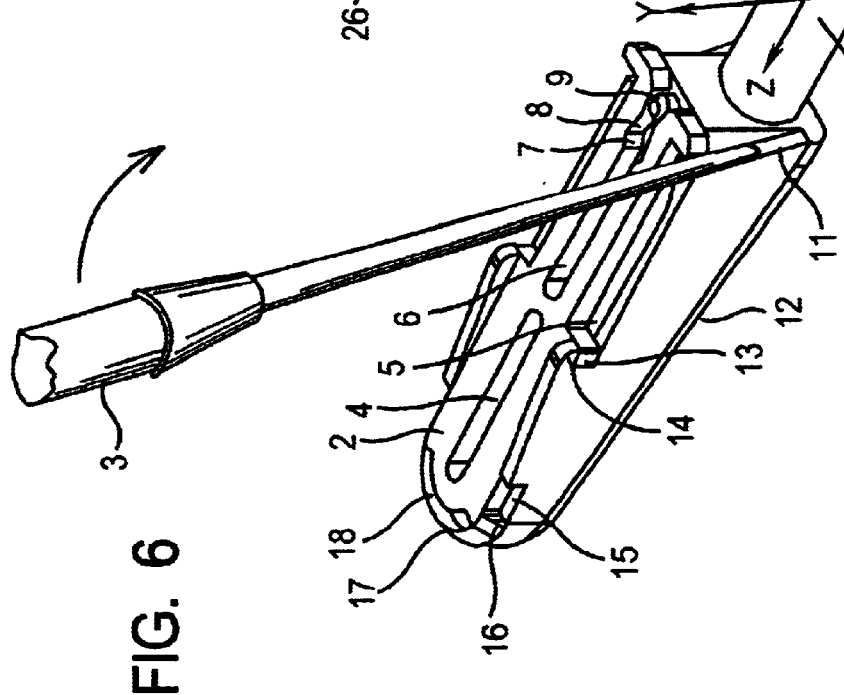
FIG. 6 is a view similar to FIG. 1 of an alternative embodiment of bone-harvesting instrument consistent with the present invention.

Referring to FIGS. 6 and 7, there is illustrated an alternative embodiment of bone-harvesting instrument in accordance with the present invention. In this embodiment, two cantilevered springs 21 provide opposing forces that cause retention cams 9 to bear on pin follower 10 forcing blade tabs 13 forward against forward travel stops 19 and thereby securely retain blade 2 in its forward most position (loaded). In this position, blade 2 is also constrained laterally by side guides 22 and vertically by the blade tabs 13 being under the hold-down tabs 14.

Referring in particular to FIG. 7, blade loading is achieved by holding the blade 2 between a finger and thumb at the spring 21 end of blade 2. Then it is placed between the side guides 22 while being angled and pulled backward causing blade catches 16 to contact back travel stops 15. In this position, insertion opening 7 is aligned with pin follower 10 and blade 2 can be lowered. Next, blade ends 23 are pushed forward with a finger or thumb causing forces to be applied to insertion cams 8 contacting pin follower 10. As more force is applied, the springs bend outwardly allowing blade 2 to move forward and eventually snap into loaded position as retention cams 9 bear on pin follower 10.

Blade removal is achieved using a prying instrument. Prying instrument 3 bears against handle pry surface 11 while it is pushed backward causing force to be applied to blade pry surface 24.

In the embodiment shown in FIGS. 6 and 7, instruments may be customized at the factory by bending reduced section 25 about the X-axis and/or Y-axis. A secure rotational grip, multiple facets, enables the surgeon to control the third degree of rotational freedom by simply gripping the handle at the desired Z-axis angle.

In use cutting edge 114 (FIG. 2) or cutting edge 17 (FIG. 6) is placed in contact with the donor bone surface and pulled backward causing graft material to be cut and flow through aperture 16 (FIG. 2) or aperture 18 (FIG. 6) into collection chamber 104 (FIG. 2) or 20 (FIG. 6).

Harvesting progress may be monitored by looking at view slot 118 (FIG. 2) or in the case of the FIG. 6 embodiment, distal view slot 4, side view slots and/or proximal view slot 6 and observing graft material in or close to the slot. These slots 5 are sufficiently narrow so as to prevent material from falling through them.

After the material is harvested, the blade may be removed, and interior volume of the collection chamber may be used as a mixing area. The mixing area may be used to mix shavings of scraped bone and blood with other materials such as xenogeneic bone, allogenic bone, alloplastic material (hydroxyapatite), platelet rich plasma, and/or recombinant growth factors (BMP) to make a composition that can be later applied to an area of a patient needing a bone graft. A curette, or other standard instrument, may be used to move the graft material from the collection chamber to a desired recipient site.

The bone-harvesting instrument of the present invention has many advantages. These include:

(1) Low cost. Only three parts are used to provide all functions:

(a) cutting edge;

(b) aperture;

(c) collection chamber;

(d) view slots;

(e) graft delivery nose;

(f) customized head angles; and (g) secure retention mechanism: guides, springs, cams, follower, stops, tabs, pry surfaces, etc.

(2) Highly secure blade retention. The angle on the face of insertion cams 8 is made shallow compared with the angle of the face on the retention cams 9. This provides relatively easy insertion and very positive retention. The prying feature allows the surgeon to easily overcome the high retention force. Additionally, handle pry surface 11 is sloped to accommodate a range of standard instrument sizes that can be used as the pry instrument 3. Thinner instruments may be positioned further down on the slope.

(3) Durable retention mechanism. Dual springs apply opposing forces to the pin follower. Thus, very little force is applied to the handle material and handle wear is minimized. The pin follower can easily be made of a material that is harder than the blade (typically Rockwell 60C v. 55C) causing the blade to be the primary wearing part. Wear on the blades cams is not significant because blades may be replaced after a few uses (typically 1 to 4) to obtain new edges.

(4) Easy blade loading. The design enables the surgeon to easily establish alignment of the small blade with the handle and to then snap it into place.

(5) View slots. Slots in the blade are used in place of a plastic window. Therefore, components are autoclaveable and reuseable.

(6) Angled head. Instruments can be readily customized at the users site by means of a flexible joint, e.g. ball and socket, or at the factory by bending reduced section 25 about the X-axis and/or the Y-axis. During surgery, the surgeon selects a handle with appropriate angles to facilitate access to the particular surgical site. Making all the handles the same, except for bends, enables them to use a common blade. Economies of scale result from producing more of the same parts. Inventory costs are also reduced.

It should be understood that, while the present invention has been described in detail herein, the invention can be embodied otherwise without departing from the principles thereof, and such other embodiments are meant to come within the scope of the present invention as defined in the following claims.

I claim:

1. A surgical instrument for scraping bone comprising:

a generally planar blade having a first end and a second end separated by a middle section, the first end having a cutting edge and an opening to allow bone shavings to pass therethrough and the middle section having at least one outwardly extending lobe;

a collection chamber for holding accumulated bone shavings having a bottom, sidewalls, and an end wall, the chamber having a upstanding retainer member for securing the at least one lobe of the blade to the collection chamber; and an elongated handle portion coupled to the end wall of the collection chamber.

2. The surgical instrument of claim 1, wherein the elongated handle portion is flexibly secured to the end wall.

3. The surgical instrument of claim 1, wherein the collection chamber comprises a mixing area for mixing the bone shavings, blood and other constituent graft materials.

4. The surgical instrument of claim 1, wherein the collection chamber and the elongated handle portion are coupled by an area of reduced mechanical strength.

5. The surgical instrument of claim 4, wherein the area of reduced mechanical strength comprises a flexible joint.

6. The surgical instrument of claim 4, wherein the area of reduced mechanical strength allows the cutting edge to be positioned at a range of angles relative to a longitudinal axis of the handle portion.

7. The surgical instrument of claim 1, wherein the collection chamber comprises a polymeric material or stainless steel.

8. The surgical instrument of claim 7, wherein the polymeric material is a medical grade plastic.

9. The surgical instrument of claim 1, wherein the collection chamber comprises a transparent or translucent plastic material.

10. The surgical instrument of claim 1, wherein the blade comprises stainless steel or monocrystalline sapphire.

11. The surgical instrument of claim 1, wherein the blade comprises a pair of opposing lobes.

12. The surgical instrument of claim 11, wherein the pair of opposing lobes are disposed adjacent an elongated longitudinal slot.

13. The surgical instrument of claim 1, wherein the middle section of the blade comprises an elongated longitudinal slot adjacent the at least one outwardly extending lobe.

14. The surgical instrument of claim 1, wherein the second end comprises a stop mechanism to restrict linear travel of the blade relative to the collection chamber.

15. The surgical instrument of claim 1, wherein the elongated handle portion is coupled to the end wall of the collection chamber through a ball and socket joint.

16. The surgical instrument of claim 1, wherein the second end comprises a stop mechanism for positioning the blade in the instrument.

17. The surgical instrument of claim 1, wherein the second end comprises a protrusion for facilitating extraction of the blade from the collection chamber.

18. The surgical instrument of claim 1, wherein the second end comprises an opening through which a prying device may be inserted to facilitate extraction of the blade from the collection chamber.

19. The surgical instrument of claim 1, wherein the upstanding retainer mechanism comprises a first cam surface, a second cam surface and a ledge portion.

20. The surgical instrument of claim 19, wherein the ledge portion helps maintain at least a portion of the blade in contact with a top surface of the collection chamber.

21. The surgical instrument of claim 20, wherein the ledge portion is spaced from the top surface approximately the thickness of the blade.

22. The surgical instrument of claim 19, wherein the first cam surface applies a first compressive force on the at least one lobe when a second compressive force is applied to the second end of the blade.

23. The surgical instrument of claim 22, wherein the first compressive force urges the at least one lobe to be displaced toward a centerline of the blade.

24. The surgical instrument of claim 23, wherein the blade comprises an elongated slot along the centerline and the at least one lobe extends into the slot when the first compressive force is applied.

25. The surgical instrument of claim 1, wherein the side walls of the collection chamber support the first end of the blade in the instrument.

26. The surgical instrument of claim 1, wherein the collection chamber further comprises a stabilizing members to restrict rotational movement of the blade in the instrument.

27. A surgical instrument for scraping bone comprising:
a blade having a first end having a cutting edge and an opening to allow bone shavings to pass therethrough;
a collection chamber for holding accumulated bone shavings having a bottom, sidewalls, and an end wall, a portion of the side wall supporting a portion of the blade; and
an elongated handle portion coupled to the end wall of the collection chamber through a flexible joint.

28. The surgical instrument of claim 27, wherein the elongated handle portion is flexibly secured to the end wall.

29. The surgical instrument of claim 27, wherein the collection chamber comprises a mixing area for mixing the bone shavings, blood and other constituent graft materials.

30. The surgical instrument of claim 27, wherein the collection chamber and the elongated handle portion are coupled by an area of reduced mechanical strength.

31. The surgical instrument of claim 30, wherein the area of reduced mechanical strength comprises a flexible joint.

32. The surgical instrument of claim 30, wherein the area of reduced mechanical strength allows the cutting edge to be positioned at a range of angles relative to a longitudinal axis of the handle portion.

33. The surgical instrument of claim 27, wherein the collection chamber comprises a polymeric material or stainless steel.

34. The surgical instrument of claim 33, wherein the polymeric material is a medical grade plastic.

35. The surgical instrument of claim 27, wherein the collection chamber comprises a transparent or translucent plastic material.

36. The surgical instrument of claim 27, wherein the blade comprises stainless steel or monocrystalline sapphire.

37. The surgical instrument of claim 27, wherein the blade comprises a pair of opposing lobes.

38. The surgical instrument of claim 37, wherein the pair of opposing lobes are disposed adjacent an elongated longitudinal slot.

39. The surgical instrument of claim 27, wherein the middle section of the blade comprises an elongated longitudinal slot adjacent the at least one outwardly extending lobe.

40. The surgical instrument of claim 27, wherein the second end comprises a stop mechanism to restrict linear travel of the blade relative to the collection chamber.

41. The surgical instrument of claim 27, wherein the elongated handle portion is coupled to the end wall of the collection chamber through a ball and socket joint.

42. The surgical instrument of claim 27, wherein the second end comprises a stop mechanism for positioning the blade in the instrument.

43. The surgical instrument of claim 27, wherein the second end comprises a protrusion for facilitating extraction of the blade from the collection chamber.

44. The surgical instrument of claim 27, wherein the second end comprises an opening through which a prying device may be inserted to facilitate extraction of the blade from the collection chamber.

45. The surgical instrument of claim 27, wherein the upstanding retainer mechanism comprises a first cam surface, a second cam surface and a ledge portion.

46. The surgical instrument of claim 45, wherein the ledge portion helps maintain at least a portion of the blade in contact with a top surface of the collection chamber.

47. The surgical instrument of claim 46, wherein the ledge portion is spaced from the top surface approximately the thickness of the blade.

48. The surgical instrument of claim 45, wherein the first cam surface applies a first compressive force on the at least one lobe when a second compressive force is applied to the second end of the blade.

49. The surgical instrument of claim 48, wherein the first compressive force urges the at least one lobe to be displaced toward a centerline of the blade.

50. The surgical instrument of claim 49, wherein the blade comprises an elongated slot along the centerline and the at least one lobe extends into the slot when the first compressive force is applied.

51. The surgical instrument of claim 27, wherein the side walls of the collection chamber support the first end of the blade in the instrument.

52. The surgical instrument of claim 27, wherein the collection chamber further comprises a stabilizing members to restrict rotational movement of the blade in the instrument.

53. A surgical instrument for scraping bone comprising:
a generally planar blade having a first end and a second end separated by a middle section, the first end having a cutting edge and an opening to allow bone shavings to pass therethrough and the middle section having at least one outwardly extending lobe, and the second end comprising a pair of cantilevered spring elements;
a collection chamber for holding accumulated bone shavings having a bottom, sidewalls, and an end wall, the chamber having a upstanding retainer member for securing the at least one lobe of the blade to the collection chamber, and a retaining mechanism for interacting with the blade spring elements; and
an elongated handle portion coupled to the end wall of the collection chamber.

54. The surgical instrument of claim 53, wherein the elongated handle portion is flexibly secured to the end wall.

55. The surgical instrument of claim 53, wherein the collection chamber comprises a mixing area for mixing the bone shavings, blood and other constituent graft materials.

56. The surgical instrument of claim 53, wherein the collection chamber and the elongated handle portion are coupled by an area of reduced mechanical strength.

57. The surgical instrument of claim 56, wherein the area of reduced mechanical strength comprises a flexible joint.

58. The surgical instrument of claim 56, wherein the area of reduced mechanical strength allows the cutting edge to be positioned at a range of angles relative to a longitudinal axis of the handle portion.

59. The surgical instrument of claim 53, wherein the collection chamber comprises a polymeric material or stainless steel.

60. The surgical instrument of claim 59, wherein the polymeric material is a medical grade plastic.

61. The surgical instrument of claim 53, wherein the collection chamber comprises a transparent or translucent plastic material.

62. The surgical instrument of claim 53, wherein the blade comprises stainless steel or monocrystalline sapphire.

63. The surgical instrument of claim 53, wherein the middle section of the blade comprises a pair of opposing lobes.

64. The surgical instrument of claim 63, wherein the pair of opposing lobes are disposed adjacent a pair of hold-down tabs formed on the collection chamber.

65. The surgical instrument of claim 53, wherein the elongated handle portion is coupled to the end wall of the collection chamber through a ball and socket joint.

66. The surgical instrument of claim 53, wherein the second end comprises a stop mechanism for positioning the blade in the instrument.

67. The surgical instrument of claim 53, wherein the second end comprises a sloped surface for facilitating extraction of the blade from the collection chamber by means of a prying device.

68. The surgical instrument of claim 53, wherein the retainer mechanism comprises a pin.

69. The surgical instrument of claim 53, wherein the side walls of the collection chamber support the first end of the blade in the instrument.

70. A blade for a bone scraping surgical instrument comprising:

a first end and a second end separated by a middle section, the first end having a cutting edge and an opening to allow bone shavings to pass therethrough and the middle section having a pair of outwardly extending lobes disposed on either side of a centrally located elongated opening.

71. The blade of claim 70, wherein the second end has a stop mechanism to limit linear travel of the blade when coupled to a cooperating collection chamber.

72. The blade of claim 70, wherein the second end has a protrusion for facilitating extraction of the blade from a cooperating collection chamber.

73. The blade of claim 70, wherein the second end has an opening through which a prying instrument can be inserted to facilitate extraction of the blade from a cooperating collection chamber.

74. The blade of claim 70, wherein the secured end comprises a pair of cantilevered spring elements.

\* \* \* \* \*